United States Patent [19]

Luly et al.

[11] Patent Number: 4,680,284
[45] Date of Patent: Jul. 14, 1987

[54] MODIFIED PHENYLALANINE PEPTIDYLAMINODIOLS

[75] Inventors: Jay R. Luly; Jacob J. Plattner, both of Libertyville; Anthony K. Fung, Waukegan, all of Ill.

[73] Assignee: Abbott Laboratories, North Chicago, Ill.

[21] Appl. No.: 818,714

[22] Filed: Jan. 16, 1986

Related U.S. Application Data

[63] Continuation-in-part of Ser. No. 693,951, Jan. 23, 1985, abandoned.

[51] Int. Cl.$^4$ .............. A61K 37/02; C07K 5/08; C07D 217/22; C07D 217/00; C07C 103/00; C07C 103/20
[52] U.S. Cl. .................. 514/18; 530/331; 546/146; 546/141; 540/476; 540/593; 540/451; 540/523; 564/153; 564/157
[58] Field of Search .............. 514/18; 530/331; 546/146, 141; 540/476, 593, 451, 523; 564/153, 157

[56] References Cited

U.S. PATENT DOCUMENTS 4,548,926 10/1985 Matsueda et al. ............. 514/19

OTHER PUBLICATIONS

Chem. Abstr., vol. 102, (1985), 91909.
Chem. Abstr., vol. 93, (1980), 205010.
Chem. Abstr., vol. 99, (1983), 122958.

*Primary Examiner*—Delbert R. Phillips
*Attorney, Agent, or Firm*—Steven F. Weinstock; Martin L. Katz

[57] ABSTRACT

The invention relates to renin inhibiting compounds of the formula:

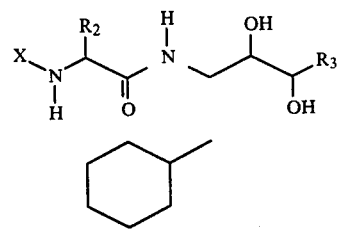

wherein $R_2$ is loweralkyl or arylalkyl; $R_3$ is loweralkyl; X is

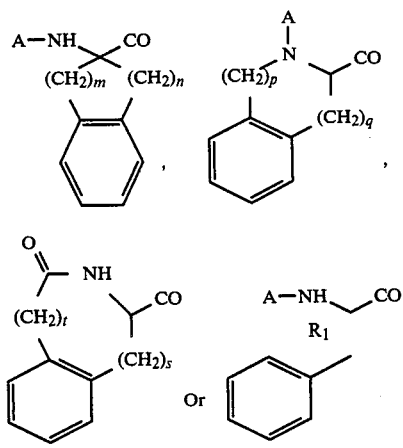

wherein A is hydrogen or an N-protecting group, $R_1$ is loweralkyl or arylalkyl, m is 1-3, n is 1-3, p is 1-3, q is 1-3, s is 1-3, and t is 0-2.

9 Claims, No Drawings

MODIFIED PHENYLALANINE PEPTIDYLAMINODIOLS

TECHNICAL FIELD

This is a continuation-in-part of U.S. patent application, Ser. No. 693,951, filed Jan. 23, 1985 now abandoned.

The present invention relates to novel organic compounds which inhibit renin, processes for making such compound, synthetic intermediates employed in these processes and method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co-workers have described polypeptide analogs containing a non-peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula:

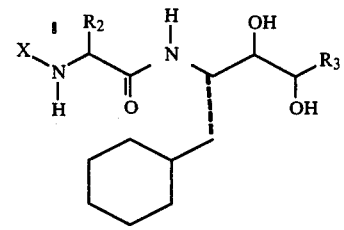

wherein $R_2$ is loweralkyl or arylalkyl; $R_3$ is loweralkyl; X is

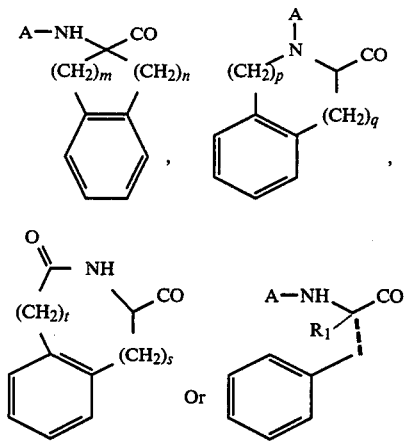

wherein A is hydrogen or an N-protecting group, $R_1$ is loweralkyl or arylalkyl, m is 1-3, n is 1-3, p is 1-3, q is 1-3, s is 1-3, and t is 0-2.

The chiral centers of the compounds of the invention may have either the "R" or "S" configuration but preferably have an "S" configuration except where noted.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), carbobenzyloxycarbonyl or benzoyl groups or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "arylalkyl" as used herein refers to an unsubstituted or substituted aromatic ring appended to an alkyl radical including but not limited to benzyl, 1- and 2-naphthylmethyl, halobenzyl (imidazol-4-yl)methyl and alkoxybenzyl.

The term "lipophilic or aromatic amino acid side chains" as used herein refers to those amino acid side chains which have an affinity for lipids or have an aromatic ring and include but are not limited to isobutyl, isopropyl, sec-butyl, benzyl, (imidazole-4-yl)methyl, p-hydroxybenzyl, 1- and 2-naphthylmethyl, and cyclohexylmethyl. The term "hydrophilic amino acid side chains" as used herein refers to those amino acid side chains which have an affinity for water and include but are not limited to hydroxymethyl, hydroxyethyl, hydroxypropyl, hydroxybutyl, aminomethyl, aminoethyl, aminopropyl, and aminobutyl. General reference to amino acid side chains in both the description and claims herein is to be taken as reference to such, whether naturally occurring in proteins or not, and to both D- and L-forms.

The terms "Ala", "His", "Leu" and "Phe" as used herein refer to alamine, histidine, leucine and phenylalanine, respectively.

The following Examples will serve to further illustrate preparation of the novel compounds of the invention.

EXAMPLE 1

2(S)-Butyloxycarbonylamino-1-cyclohexyl-6-methylhept-3-ene

To a stirred −78° C. solution of Boc-cyclohexylalanine methyl ester (40 g, 140 mmol) in anhydrous toluene (250 ml) was added diisobutylaluminum hydride (130M%, 1.5M solution in toluene, 121.4 ml) at a rate to keep the internal temperature below −60° C. After stirring for an additional 20 minutes at −78° C., the aldehyde solution is used immediately as described below.

To a potassium hydride (35% dispersion in oil, 32.09 g) suspension in a 0° C. mixture of anhydrous tetrahydrofuran/dimethyl sulfoxide (THF/DMSO) (1000 ml/200 ml) under dry $N_2$ was added 1,1,1,3,3,3-hexamethyldisilazane (209M%, 49.07 g) dropwise. After stirring at 0° C. for 1 hour, the resulting solution was added via cannula to a 0° C. flask containing isopentyltriphenylphosphonium bromide (209M%, 125.66 g). The mixture was stirred vigorously for 1 hour at which time it was cooled to −78° C. The −78° C. aldehyde solution prepared above was then added via cannula. After stirring at −78° C. for 15 minutes, the mixture was allowed to slowly warm to room temperature and then heated to 40° C. for 12 hours. The mixture was then cooled to room temperature and quenched with methanol (7.65 ml) followed by aqueous Rochelle salts (100 ml saturated solution and 500 ml $H_2O$). The mixture was then extracted with ethyl acetate (2×). The combined extracts were washed with water and brine. Drying ($MgSO_4$) and evaporating provided crude alkene which was chromatographed on silica gel (ether/hexane) to give 16.5 (38%) of the desired compound as an 85:15 mixture of cis:trans isomers. Mp=53°–55° C. Mass spectrum: $M^+ = 309$.

Anal. calcd. for $C_{19}H_{35}NO_2$: C73.7; H, 11.4; N, 4.5. Found: C, 73.8; H, 11.4; N, 4.5.

EXAMPLE 2

2(S)-t-Butyloxycarbonylamino-1-cyclohexyl-3,4-dihydroxy-6-methylheptane: The 3(R)4(S), 3(S)4(S), 3(R)4(R), and 3(S)4(R) Diastereomers To a solution of the resultant compound of Example 1 (8.50, 27.5 mmol) in dry THF (150 ml) were added $OsO_4$ (2.8 ml of a 2.5% solution in t-butanol) and N-methylmorpholine N-oxide (9.28 g, 68.7 mmol). After 4 days the mixture was partitioned between ether (200 ml) and brine (100 ml). The aqueous layer was back-extracted with ether (2×100 ml), and the combined organic phase was washed with 10% $Na_2SO_3$, 0.1M $H_3PO_4$, and brine. Drying ($MgSO_4$) and evaporating provided a residue (10.81 g) which was chromatographed on silica gel to elute a 60% yield of the 4 diols in the following order.

3(R),4(S) Mass spectrum: $(M+H)^+ = 344$. Anal. calcd. for $C_{19}H_{37}NO_4$: C, 66.4; H, 10.9; N, 4.1. Found: C, 66.4; H, 10.8; N, 3.9.

3(S),4(S) Mass spectrum: $(M+H)^+ = 344$. Anal. calcd. for $C_{19}H_{37}NO_4$: C, 66.4; H, 10.9; N, 4.1. Found: C, 66.4; H, 11.1; N, 4.0.

3(R),4(R) Mass spectrum: $(M+H)^{30} = 344$.

3(S),4(R) Mass spectrum: $(M+H)^+ = 344$, Anal. calcd. for $C_{19}H_{37}NO_4$: C, 66.4; H, 10.9; N, 4.1. Found: C, 66.0; H, 10.7; N, 4.0.

EXAMPLE 3

Boc-His Amide of 2(S)-Amino-1-cyclohexyl-3(R),4(S)-dihydroxy-6-methylheptane

The 3(R),4(S) diastereomer of Example 2 (1.26 g, 3.67 mmol) was treated with 2.3M $HCl/CH_3OH$ (32 ml, anhydrous) for 16 hours at which time evaporation and vacuum drying provided the corresponding amine hydrochloride (1.01 g, 98%).

To a stirred −20° C. solution of the above salt (0.60 g, 2.1 mmol), Boc-His (0.548 g), 1-hydroxybenzotriazole (HOBT, 0.43 g), and N-methylmorpholine (0.239 g) was added 1,3-dicyclohexylcarbodiimide (DCC, 0.442 g). The mixture was warmed to room temperature over 3 hours and then stirred for an additional 18 hours. The mixture was diluted with ethyl acetate and washed with saturated aq. $NaHCO_3$ and brine. Drying and evaporating provided a solid which was recrystallized to give the desired compound (0.51 g, 50%, 2 crops). Mass spectrum: $M^+ = 480$.

Anal. calcd. for $C_{25}H_{44}N_4O_5.\frac{3}{4}H_2O$: C, 60.8; H, 9.1; N, 11.3. Found: C, 60.9; H, 9.2; N, 11.0.

EXAMPLE 4

2-Ethoxycarbonylaminoindan-2-carboxylic Acid (EtOC-AICA)

To a stirred refluxing mixture of 2-aminoindan-2-carboxylic acid (1.90 g, 10.7 mmol, Pinder, R. M.; Butcher, B. H.; Buxton, D. A.; and Howells, O. J. *J. Med. Chem.* 1971, 14, 892) in ethyl acetate (200 ml) ws added ethyl chloroformate (1.16 g, 10.7 mmol). After 15 hours, the mixture was cooled, filtered, evaporated, and vacuum dried to give 1.17 g (44%) of a white solid.

EXAMPLE 5

EtOC-AICA-His Amide of 2(S)-Amino-1-cyclohexyl-3(R),4(S)-dihydroxy-6-methylheptane The resultant compound of Example 3 (50 mg, 0.104 mmol) was deprotected with 2.2M HCl/CH$_3$OH (6 ml, anhydrous). Evaporation after 6 hours provided the corresponding amine dihydrochloride.

To a stirred $-12°$ C. solution of the resultant compound of Example 4 (25.9 mg, 0.104 mmol, EtOC-AICA-OH) and N-methylmorpholine (10.5 mg) in dry THF was added isobutylchloroformate (14.4 mg). After 3 minutes, the above salt and N-methylmorpholine (21 mg) in dry DMF was added. The mixture was warmed to room temperature for 3 hours, diluted with ethyl acetate and washed sequentially with brine, saturated, aq. NaHCO$_3$, and brine. Dryng and evaporating provided a residue which was chromatographed on silica gel eluting with dichloromethane/methanol mixtures to give 30 mg (48%) of the desired compound. Mass spectrum: $(M+H)^+ = 612$.

EXAMPLE 6

N-Carboxy-2-aminoindan-2-carboxylic Acid Anhydride

The resultant compound of Example 4 (500 mg, 2.00 mmol) was dissolved in thionyl chloride (3 ml). Evaporation after 17 hours provided a solid which was recrystallized from ethyl acetate/hexane to give 239 mg (59%) of the desired product.

EXAMPLE 7

AICA-His Amide of 2(S)-Amino-1-cyclohexyl-3(R),4(S)-dihydroxy-6-methylheptane To a stirred 0° C. solution of the amine dihydrochloride prepared in Example 5 (0.104 mmol) and triethylamine (21.0 mg) in dry DMF (5 ml) was added a solution of the resultant compound of Example 6 (21.1 mg, 0.104 mmol) in DMF (0.5 ml). After 16 hours, the mixture was diluted with saturated, aq. NaHCO$_3$ (10 ml) and extracted with ethyl acetate several times. The combined organic phase was washed (brine), dried (Na$_2$SO$_4$), filtered, and evaporated to a solid which was purified by silica gel chromatography (dichloromethane/methanol) to give 28 mg (50%) of the desired compound. Mass spectrum: $(M+H) = 540$.

Anal. calcd. for C$_{30}$H$_{45}$N$_5$O$_4$: C, 66.8; H, 8.4; N, 13.0. Found: C, 67.1; H, 8.5; N, 13.0.

EXAMPLE 8

2(R,S)-Amino-1,2,3,4-tetrahydronaphthalene-2-carboxylic Acid, (R,S-ATCA)

A stirred suspension of 7,8-benzo-1,3-diazaspiro[4.5]-decane-2,4-dione (1.73 g, 8.00 mmol) and Ba(OH)$_2$.8H$_2$O in water (12 ml) was heated in a sealed tube at 190° C. for 2 hours. The suspension was then filtered while warm. The solids were washed with water, and the combined aqueous phase was treated with ammonium carbonate. Filtration, evaporation, re-solution, and lyopholization provided 0.44 g (29%) of the corresponding amino acid. Mass spectrum: $(M+H)^+ = 192$.

EXAMPLE 9

2(R,S)-Ethoxycarbonylamino-1,2,3,4-tetrahydronaphthalene-2-carboxylic Acid (EtOC-(R,S)-ATCA)

To a stirred 0° C. solution of the resultant compound of Example 8 (250 mg, 1.31 mmol) in 1M NaOH/1M NaHCO$_3$ (1.31 ml/2.62 ml) was added ethoxycarbonyl-O-hydroxysuccinimide ester (245 mg, 1.31 mmol) in dioxane (2.6 ml). After 22 hours, the mixture was acidified (2M HCl) and extracted (ethyl acetate, 3×10 ml). The combined organic phase was washed (water 3×, brine 2×), dried (NaSO$_4$), filtered, and evaporated to a residue which was chromatographed on silica gel (dichloromethane, methanol) to give 183 mg (53%) of the desired compound. Mass spectrum: $M^+ = 263$.

Anal. calcd. for C$_{14}$H$_{17}$NO$_4$: C, 63.8; H, 6.5; N, 5.3. Found: C, 63.4; H, 6.4., N, 5.5.

EXAMPLE 10

EtOC-(R,S)-ATCA-His Amide of 2(S)-Amino-1-cyclohexyl-3(R),4(S)-dihydroxy-6-methylheptane Following the procedure of Example 5, but replacing the resultant product of Example 4 with the resultant product of Example 9, gave the desired product. Mass spectrum: $(M+H)^+ = 626$.

EXAMPLE 11

(R,S)-ATCA-His Amide of 2(S)-Amino-1-cyclohexyl-3(R),4(S)-dihydroxy-6-methylheptane Using the procedure of Example 6, but replacing the resultant product of Example 4 with the resultant product of Example 9, gave the corresponding anhydride derivative. Following the procedure of Example 7, but replacing the anhydride derivative of Example 6 with the above anhydride derivative, gave the desired product.

EXAMPLE 12

2-Ethoxycarbonyl-1,2,3,4-tetrahydro-3(R,S)-isoquinolinecarboxylic Acid (EtOC-TIC)

Following the procedure of Example 9, but replacing the resultant compound of Example 8 with 1,2,3,4-tetrahydro-3-(R,S)-isoquinolinecarboxylic acid hydrochloride, gave the desired product.

EXAMPLE 13

EtOC-TIC-His Amide of 2(S)-Amino-1-cyclohexyl-3(R),4(S)-dihydroxy-6-methylheptane Following the procedure of Example 5, but replacing the resultant compound of Example 4 with the resultant compound of Example 12, gave the desired product. Mass spectrum: $(M+H)^+ = 612$.

EXAMPLE 14

1-Oxo-1,2,3,4-tetrahydro-3(R,S)-isoquinolinecarboxylic Acid (OTIC-OH)

To a solution of sodio diethyl acetamidomalonate (0.046 mol) in ethanol (125 ml) was added o-cyanobenzyl bromide (9 g, 0.046 mol) all at once. The reaction was stirred overnight at room temperature and then distributed between ether and aqueous NaCl. Drying and evaporating gave a solid product. A 1.5 g sample of this material was heated at reflux for 3 hours with 25 ml of 48% HBr. After cooling, the mixture was diluted with aqueous NaCl and was extracted with ethyl acetate. The organic extract was washed, dried, and evaporated to give 250 mg of product, mp 235°–238° C. Anal. calcd. for $C_{10}H_9NO_3$: C, 62.82; H, 4.74; N, 7.33. Found: C, 61.69; H, 4.78; N, 7.11.

EXAMPLE 15

OTIC-His Amide of 2(S)-Amino-1-cyclohexyl-3(R),4(S)-dihydroxy-6-methylheptane

Following the procedure of Example 5, but replacing the resultant compound of Example 4 with the resultant compound of Example 14, gave the desired compound. Mass spectrum: $(M+H)^+ = 554$.

Anal. calcd. for $C_{30}H_{43}N_5O_5 \cdot \frac{1}{2}H_2O$: C, 64.0; H, 7.9; N, 12.4. Found: C, 63.7; H, 8.4; N, 11.8.

EXAMPLE 16

2(S)-Ethoxycarbonylamino-2-methyl-3-phenylpropionic Acid (EtOC-AMPA-OH)

Following the procedure of Example 9, but replacing the resultant compound of Example 8 with 2(S)-amino-2-methyl-3-phenylpropionic acid, gave the desired compound. Mass spectrum: $M^+ = 251$.

EXAMPLE 17

AMPA-His Amide of 2(S)-Amino-1-cyclohexyl-3(R),4(S)-dihydroxy-6-methylheptane

Using the procedure of Example 6, but replacing the resultant product of Example 4 with the resultant product of Example 16, gave the corresponding anhydride derivative. Following the procedure of Example 7, but replacing the anhydride derivative of Example 6 with the above anhydride derivative, gave the desired product. Mass spectrum: $(M+H)^+ = 541$.

EXAMPLE 18

4(S)-Benzyl-2,4-dimethyloxazol-5-one

2(S)-Acetylamino-2-methyl-3-propionic acid (0.68 g) was refluxed in acetic anhydride (5 ml) for 5 hours. Evaporation under high vacuum gave the desired product in quantitative yield which was used in the next step without further purification.

EXAMPLE 19

Acetyl-AMPA-His Amide of 2(S)-Amino-1-cyclohexyl-3(R),4(S)-dihydroxy-6-methylheptane Following the procedure of Example 7, but replacing the resultant compound of Example 6 with the resultant compound of Example 18, gave the desired product. Mass spectrum: $(M+H)^+ = 584$.

EXAMPLE 20

N-Carboxy-2-amino-2,2-dibenzylacetic Acid Anhydride

Following the procedure of Example 6, but replacing the resultant compound of Example 4 with 2-benzyloxycarbonylamino-2,2-dibenzylacetic acid (Cbz-ADBA-OH), gave the desired compound. Mass spectrum: $M^+ = 281$.

EXAMPLE 21

ADBA-His Amide of 2(S)-Amino-1-cyclohexyl-3(R),4(S)-dihydroxy-6-methylheptane

Using the procedure of Example 6, but replacing the resultant product of Example 4 with the resultant product of Example 20, gave the corresponding anhydride derivative. Following the procedure of Example 7, but replacing the anhydride derivative of Example 6 with the above anhydride derivative, gave the desired product.

The compounds of the present invention can be used in the form of salts derived from inorganic or organic acids. These salts include but are not limited to the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl., and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-5}$ to $10^{-9}$M as seen in Table I.

TABLE I

| Example Number | $IC_{50}$ (nM) |
| --- | --- |
| 5 | 15 |
| 7 | 300 |
| 10 | 5 |
| 13 | 10 |
| 15 | 100 |
| 17 | 10 |
| 19 | 9 |
| 21 | 25 |

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, of infusion techniques.

Injectable preparation, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer s solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foreoging is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A renin inhibiting compound of the formula:

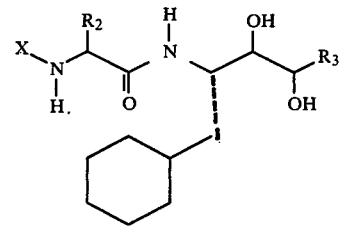

wherein $R_2$ is loweralkyl or arylalkyl; $R_3$ is loweralkyl; X is

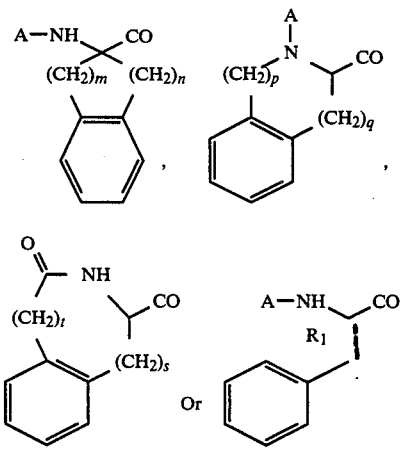

wherein A is hydrogen or an N-protecting group, $R_1$ is loweralkyl or arylalkyl, M is 1-3, m is 1-3, p is 1-3, q is 1-3, s is 1-3, and t is 0-2 and pharmaceutically acceptable salts thereof.

2. The renin inhibiting compound of claim 1 wherein x is

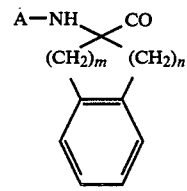

3. The renin inhibiting compound of claim 2 wherein A is ethoxycarbonyl, n is 1 and m is 2.

4. The renin inhibiting compound of claim 1 wherein X is

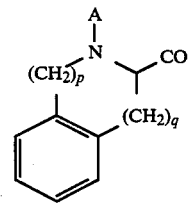

5. The renin inhibiting compound of claim 4 wherein A is ethoxycarbonyl, p is 1 and q is 1.

6. The renin inhibiting compound of claim 1 wherein X is

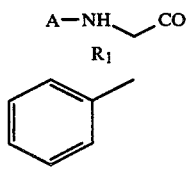

7. The renin inhibiting compound of claim 6 wherein A is hydrogen and $R_1$ is methyl.

8. A pharmaceutical composition for treating renin-associated hypertension, comprising a pharmaceutical carrier and a therapeutically effective amount of the compound of the formula:

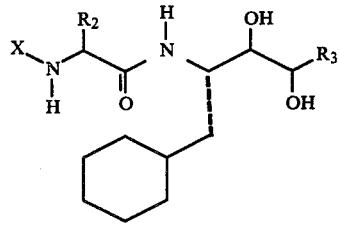

wherein $R_2$ is loweralkyl or arylalkyl; $R_3$ is loweralkyl; X is

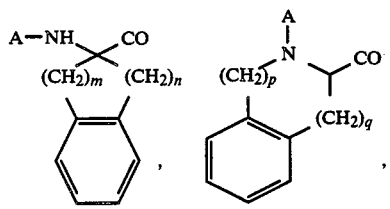

-continued

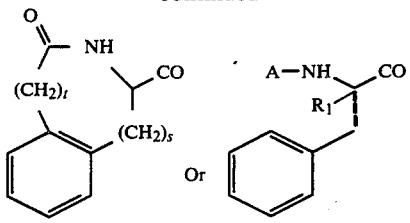

wherein A is hydrogen or an N-protecting group, $R_1$ is loweralkyl or arylalkyl, m is 1–3, n is 1–3, p is 1–3, q is 1–3, s is 1–3, and t is 0–2 and pharmaceutically acceptable salts thereof.

9. A method of treating hypertension comprising administering to a host in need of such treatment a therapeutically effective amount of a compound of the formula:

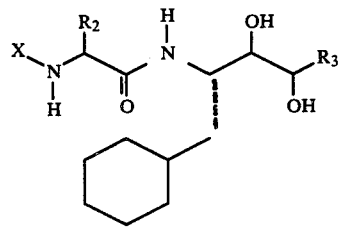

wherein $R_2$ is loweralkyl or arylalkyl; $R_3$ is loweralkyl; X is

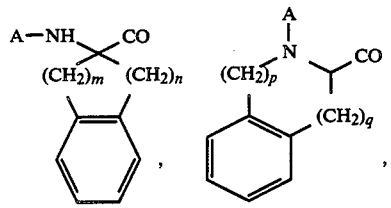

wherein A is hydrogen or an N-protecting group, $R_1$ is loweralkyl or arylalkyl, m is 1–3, n is 1–3, p is 1–3, q is 1–3, s is 1–3, and t is 0–2 and pharmaceutically acceptable salts thereof.

* * * * *

UNITED STATES PATENT AND TRADEMARK OFFICE
CERTIFICATE OF CORRECTION

PATENT NO. : 4,680,284
DATED : July 14, 1987
INVENTOR(S) : J. Luly, et al.

It is certified that error appears in the above—identified patent and that said Letters Patent is hereby corrected as shown below:

In claim 6, the structure: the dotted line is missing and should be inserted as follows:

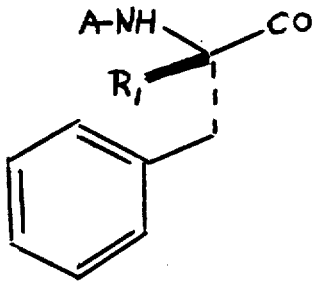

Signed and Sealed this

Fifth Day of January, 1988

Attest:

DONALD J. QUIGG

Attesting Officer

Commissioner of Patents and Trademarks